(12) United States Patent
Lin et al.

(10) Patent No.: US 9,737,890 B2
(45) Date of Patent: Aug. 22, 2017

(54) MICROFLUIDIC DEVICE AND METHOD FOR OPERATING THEREOF

(71) Applicant: Shaoxing PushKang Biotechnology Co., Ltd., Shaoxing, Zhejiang Province (CN)

(72) Inventors: Chia-Hui Lin, Shaoxing (CN); Bo Yu, Shaoxing (CN); Yi-Feng Yang, Shaoxing (CN)

(73) Assignee: SHAOXING PUSHKANG BIOTECHNOLOGY CO., LTD., Shaoxing, Zhejiang Province (CN)

( * ) Notice: Subject to any disclaimer, the term of this patent is extended or adjusted under 35 U.S.C. 154(b) by 214 days.

(21) Appl. No.: 14/556,219

(22) Filed: Nov. 30, 2014

(65) Prior Publication Data

US 2016/0051986 A1 Feb. 25, 2016

(30) Foreign Application Priority Data

Aug. 20, 2014 (TW) .............................. 103128617 A

(51) Int. Cl.
*G01N 35/00* (2006.01)
*B01L 3/00* (2006.01)
*G01N 33/483* (2006.01)

(52) U.S. Cl.
CPC ..... *B01L 3/502738* (2013.01); *B01L 3/50273* (2013.01); *G01N 33/483* (2013.01); *B01L 2200/0605* (2013.01); *B01L 2200/0621* (2013.01); *B01L 2300/0803* (2013.01); *B01L 2300/087* (2013.01); *B01L 2300/0864* (2013.01); *B01L 2400/0409* (2013.01); *B01L 2400/0433* (2013.01)

(58) Field of Classification Search
None
See application file for complete search history.

(56) References Cited

U.S. PATENT DOCUMENTS

2013/0196360 A1\* 8/2013 Yeo ..................... G01N 21/276
435/28

\* cited by examiner

*Primary Examiner* — Robert Xu
(74) *Attorney, Agent, or Firm* — Cheng-Ju Chiang

(57) ABSTRACT

The present invention provides a microfluidic device which comprises a drive module and a microfluidic platform. The drive module further comprises a rotary unit and a vibration unit for driving the microfluidic platform, and the microfluidic platform further comprises multiple microfluidic elements for performing tests. The present invention also provides a method for operating a microfluidic device. The method comprises steps using the rotary unit and steps using the vibration unit to distribute sample in a microfluidic structure.

7 Claims, 11 Drawing Sheets

MICROFLUIDIC DEVICE AND METHOD FOR OPERATING THEREOF

1. TECHNICAL FIELD

Some embodiments of the present invention provide microfluidic devices and methods for operating thereof. More particularly, some embodiments of the present invention provide devices and methods for delivering fluid under a rotary system.

2. DESCRIPTION OF THE RELATED ART

Sample preparation and sample volume metering are highly complex tasks in the art of analysis; both require well-trained technicians and advanced instruments to perform the tasks. Sample preparation and sample volume metering are important for obtaining qualified samples for analysis. However, costs on training technicians and investing instruments built a high barrier to found an analysis laboratory. Large institutes such as research centers and hospitals may be capable of affording an analysis department, but local workshops and clinics, standing on the first line, lack the ability to own a private laboratory. Those local workshops and clinics usually outsource the tasks including inspection, verification, and testing to professional laboratories. Nevertheless, extra transit time to those professional laboratories may lead to shortcomings includes being time-consuming and increasing the possibility of sample denaturation.

Recent development in the field of lab-on-a-chip (LOC) successfully compromises the above-mentioned shortcomings. Typical advantages of an LOC are the low fluid volumes consumption, low fabrication costs, fast analysis, and high portability. The LOC technology soon becomes an important part of efforts to improve global health, particularly through the development of point-of-care testing (POCT) devices. The LOC technology promises a future allowing healthcare providers in poorly equipped clinics to perform diagnostic tests locally. Similar to conventional technologies, sample preparation and sample volume metering are important procedures to enhance accuracy of the LOC-based devices.

Prior arts commercially available on the market usually provide rough, inconsistent results since those LOC-based devices lack for the ability to perform sample preparation. For example, cholesterol meters and glucometers commonly seen in life are small and portable devices which are convenient to use. However, those LOC-based devices, using crude clinical samples as subjects and transporting the samples in device by capillary siphoning, provide rough results with low specificity. The accuracy is not qualified for medical institutes which require accurate data to determine the medical condition for a patient.

One common sample preparation is centrifugation. Centrifugation provides a fast but low-cost way to purify crude samples. Centrifugation utilizes the centrifugal force and density of substances to isolate subsamples. This preliminary procedure may significantly elevate the accuracy of following assays. For example, the EPA staff may use centrifugation to separate the suspended solids from a water sample and provides the supernatant for colorimetric analysis. In another example, a laboratory technician may use centrifugation to isolate the precipitated particles from a urine sample and exams the presence of crystalluria in the precipitated particles under a microscope.

Sample volume metering is another important procedure to the LOC technology. In the field of bioanalysis, volumetric measurements are usually applied on samples and reagents to reduce variations and provide stable and accurate test results. For example, in a control experiment, standard curves or reference values may be established from the positive controls and negative controls before determining the value of an unknown sample. The common prerequisite of a control experiment is that the control samples and unknown samples are reacted under the same condition, such as in the same volume or under the same temperature.

The LOC-based devices commercially available on the market, however, show deficiency of the ability to perform high-quality volume metering. Typical methods for volume metering may be classified into manual category or automate category. The manual category, due to the possible manmade errors, hardly provides solutions in a consistent volume and usually induces variations in the following assays. For example, triglyceride levels in blood are considered to be below 200 mg/dL in a health adult. In a standard 6-μL protocol, injecting 8 μL of blood sample into the detection chamber of a LOC-based device would result in significant differences. A subject with a triglyceride level of 180 mg/dL would be diagnosed as one at high risk since the result indicates that the triglyceride level of the subject is 240 mg/dL. The automate category, on the other hand, usually uses capillary siphoning or wax plug to control distribution of solution. The capillary siphoning and wax plug are nevertheless highly unstable and hard to fabricate.

Accordingly, there is a need for a LOC-based device which is easy to be fabricated and featured with high stability and low-cost.

SUMMARY

Some embodiments of the present invention disclosed herein provide microfluidic devices and methods for operating the microfluidic devices. In particular, the microfluidic device in at least one embodiment has been developed to provide with high stability and low-cost. The microfluidic device may perform assays with a small volume of sample and produce consistent, reliable results in a short time. The microfluidic device utilizes rotation and vibration for sample preparation and sample volume metering and therefore provide qualified samples for assays.

In some embodiments, a microfluidic device is provided. The microfluidic device comprises a drive module and a microfluidic platform. The microfluidic platform may be mounting on the drive module for use. The drive module itself contains a rotary unit and a vibration unit, and is configured for driving and controlling movement of the microfluidic platform. The microfluidic platform has a center of rotation and a least one microfluidic element, and is configured for sample preparation and sample volume metering. The microfluidic element comprises an injection chamber, a metering chamber, and a reaction chamber. The injection chamber is configured for accommodating samples. The metering chamber is connected with the injection chamber and is configured for sample preparation and sample volume metering. The reaction chamber is connected with the metering chamber and is configured for receiving samples from the metering chamber. The reaction chamber may also accommodate a test strip for performing in situ assays.

In some embodiments, a method for operating microfluidic devices is provided. In the first step, a sample and a test strip may be placed into the injection chamber and the reaction chamber of a microfluidic platform respectively. The microfluidic platform subsequently starts rotating and drive the sample to flow from the injection chamber to a metering chamber. The microfluidic platform then vibrates to transfer the sample from the metering chamber into that reaction chamber containing a test strip. The contact between the sample and the test strip initiates reactions and the results of reaction may be examined by a detection module or the user.

Some embodiments of the present invention are characterized in the efficacy of sample preparation. Subsamples used for an assay may be isolated from the injected sample rapidly with the rotary unit (i.e., a rotary engine) of the microfluidic device. Utilizing the centrifugal force and density of matters, a short centrifugation may successfully segregate the high density substances and low density substances in the injected sample. This quick subsampling provides in situ sample purification and largely improves the accuracy.

Some embodiments of the present invention are characterized in the stability and reproducibility. The low density substances derived from the injected sample may be transferred from the metering chamber to the reaction chamber by using the vibration unit (i.e., a vibration motor) of the microfluidic device. The vibration unit drives the platform to vibrate, shake, or repeatedly switch between clockwise and counterclockwise rotations. With the automate method, man-made errors and variations are largely reduced. For example, using the vibration unit to transfer the sample to reaction chambers on a same microfluidic platform at a time may provide consistent reaction conditions and elevate the stability and reproducibility.

Some embodiments of the present invention are characterized in that the sample volume transferred from the metering chamber to the reaction chamber is manageable. The transferred volume is determined by several variables including the shape of the metering chamber, the capacity of the metering chamber, the distance between the metering chamber and the center of rotation, and the injected volume of sample. Manipulating vibration condition of the vibration unit provides an alternate way to manage the transferred volume.

The microfluidic devices in some embodiments are capable of performing assays with a small sample volume. Fabrication of the microfluidic devices is simple and the cost is affordable. The microfluidic devices may produce consistent, reliable results in a short time. Several embodiments herein may apply to fields including chemical testing, biochemical testing, medical testing, water testing, environmental testing, food inspection, and the defense industry.

DESCRIPTION OF THE PREFERRED EMBODIMENTS

At least one embodiment of the present invention provides a microfluidic device comprising a drive module and a microfluidic platform. The drive module contains a rotary unit and a vibration unit, and is configured for driving and controlling movement of the microfluidic platform. The microfluidic platform has a center of rotation and a least one microfluidic element, and is configured for sample preparations. The microfluidic platform may be mounting on the drive module for use. The microfluidic element further comprises an injection chamber, a metering chamber, and a reaction chamber.

Figure 1A:
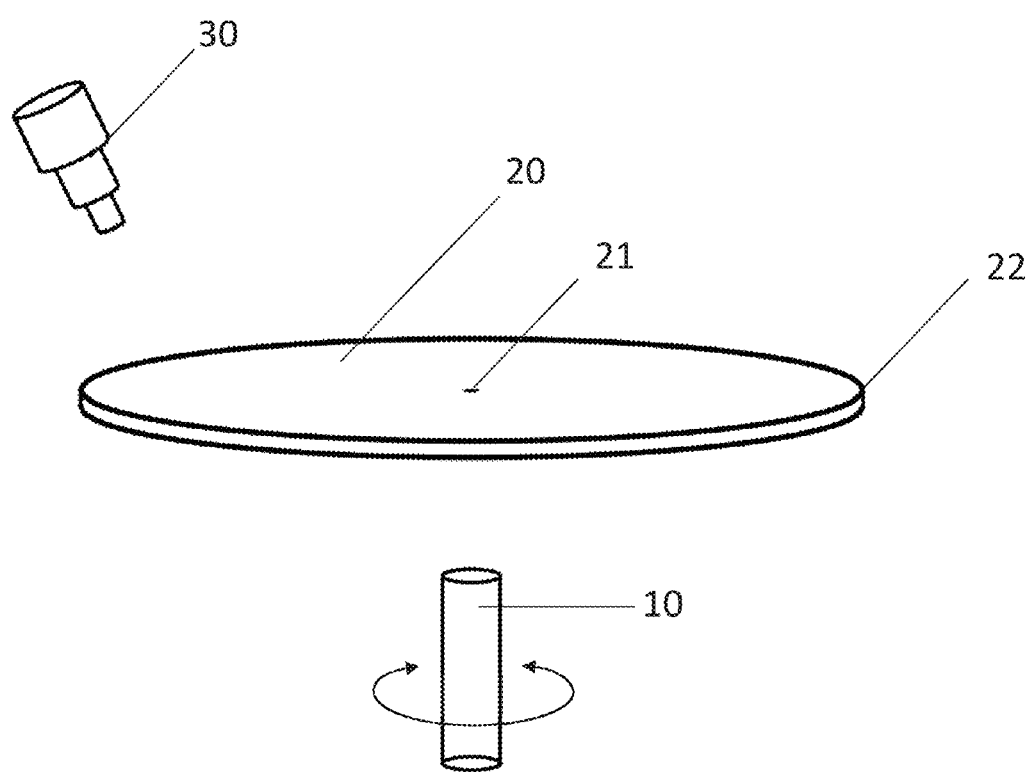
FIG. 1A is a schematic diagram illustrating a microfluidic device, according to some embodiments of the present invention.
Figure 1B:
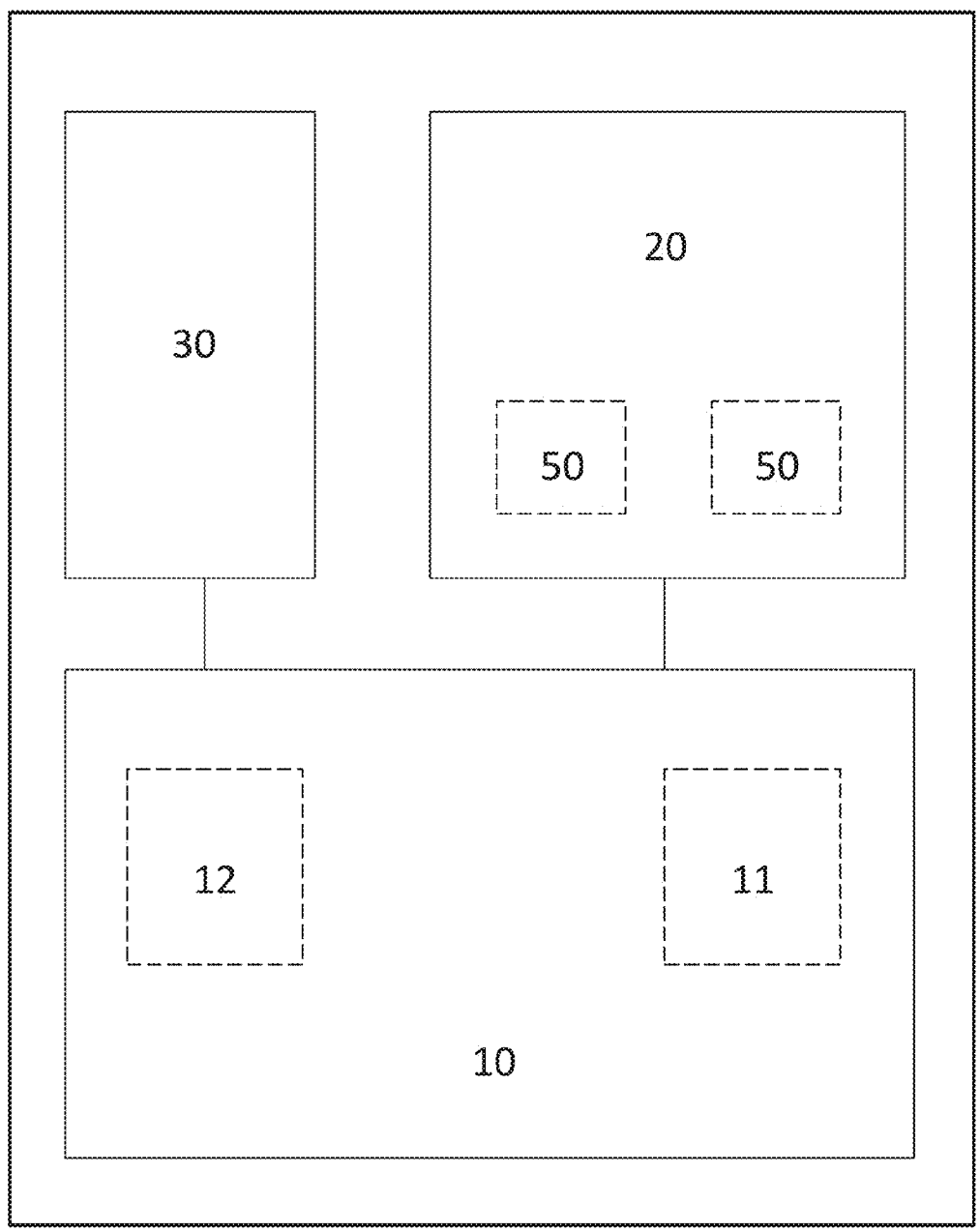
FIG. 1B is a block diagram illustrating the connections between the exemplary components of a microfluidic device, according to some embodiments of the present invention.

FIG. 1A and FIG. 1B are the schematic diagram and block diagram illustrating a microfluidic device according to some embodiments of the present invention. The microfluidic device comprises a drive module 10 and a microfluidic platform 20. The microfluidic platform 20 may be mounting on the drive module 10 for use, since the drive module 10, containing a rotary unit 11 and a vibration unit 12, is configured for driving and controlling movement of the microfluidic platform 20. The microfluidic platform contains a center of rotation 21 and a circumference 22, and is configured for sample preparations. As illustrated in FIG. 1B, the microfluidic platform 20 further comprises at least one microfluidic element 50.

The drive module 10 illustrated in FIG. 1A may be a centrifuge comprising a rotary unit 11 and a vibration unit 12. An activated drive module 10 may induce the microfluidic platform 20 to rotate, vibrate, or switch repeatedly between clockwise and counterclockwise rotations.

The microfluidic platform 20 in FIG. 1A may be formed in a circular, square, polygonal, or other radially symmetrical shapes. The material of the microfluidic platform 20 may be one selected from the group consisting of polyethylene, polyvinyl alcohol, polypropylene (PP), polystyrene, polycarbonate, polymethylmethacrylate (PMMA), polydimethylsiloxane, silicon dioxide and the combination thereof.

As illustrated in FIG. 1A and FIG. 1B, a detection module 30 may be further comprised in the microfluidic device. The detection module 30 may connect to the drive module 10, and is configured for obtaining or sensing signals such as the test results in the microfluidic device. The detection module 30 may, for example, be one selected from the group consisting of a spectrophotometer, a colorimeter, a turbidimeter, a thermometer, a pH meter, an ohmmeter, a colonometer, a sensor image sensor, and the combinations thereof.

Figure 2A:
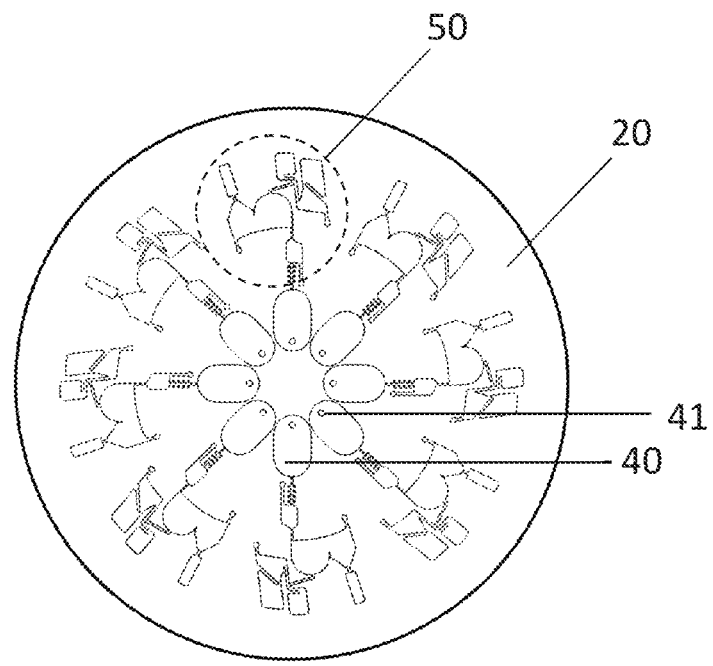
FIG. 2A is a schematic diagram illustrating a microfluidic platform having isolated microfluidic elements, according to some embodiments of the present invention.

FIG. 2A is a schematic diagram illustrating a microfluidic platform having isolated microfluidic elements, according to some embodiments of the present invention. The microfluidic platform 20 comprises several isolated microfluidic elements 50, and each microfluidic elements 50 further comprises an injection chamber 40 and an injection port 41. The microfluidic elements 50 on the microfluidic platform 20 may each accommodates a sample and performs an assay independently.

Figure 2B:
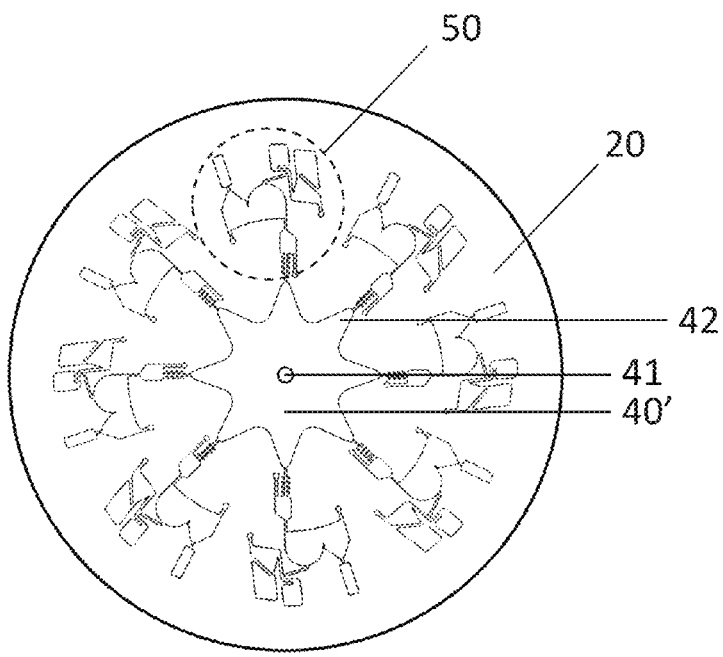
FIG. 2B is a schematic diagram illustrating a microfluidic platform having integrated microfluidic elements, according to some embodiments of the present invention.

FIG. 2B is a schematic diagram illustrating a microfluidic platform having integrated microfluidic elements, according to some embodiments of the present invention. The microfluidic platform 20 comprises an injection chamber 40', an injection port 41, multiple sub-chambers 42, and multiple microfluidic elements 50. The injection chamber 40' is configured on the center of the microfluidic platform 20 and connects with the multiple microfluidic elements 50 via the multiple sub-chambers 42. Once a sample is injected through the injection port 41, the sample may be distributed to every microfluidic element 50 evenly via the sub-chambers 42. The microfluidic platform 20 may perform multiple assays simultaneously.

Some embodiments of the present invention may combine the features of FIG. 2A and FIG. 2B to generate a microfluidic platform 20 with multiple groups of microfluidic elements 50. For instance, an embodied microfluidic platform may comprise four pairs of microfluidic elements, and the two microfluidic elements in a pair are integrated by sharing a same injection chamber. Once a sample is injected into an injection chamber, the sample may be distributed to two microfluidic elements evenly via the sub-chambers connected between the injection chamber and the two microfluidic elements. A pair of microfluidic elements may perform two assays for a same sample simultaneously.

Figure 3A:
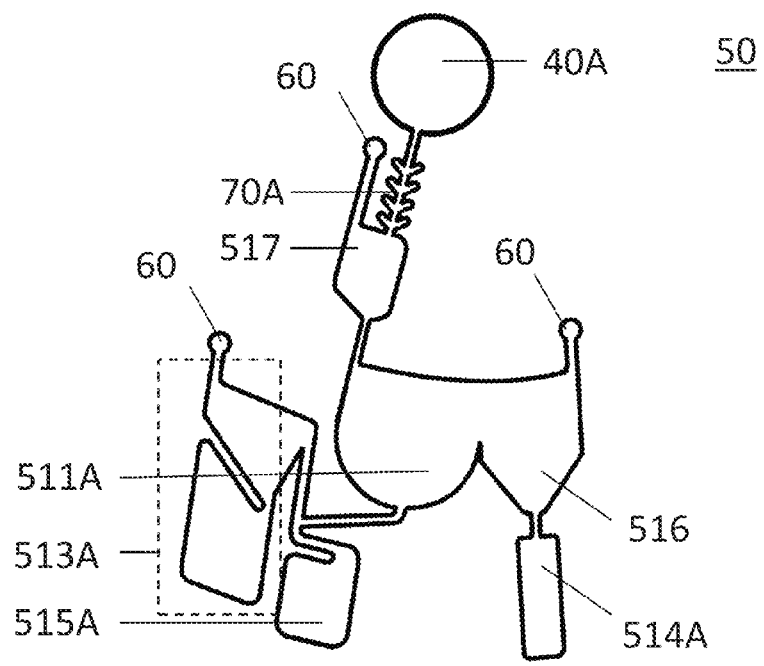
FIG. 3A is a schematic diagram illustrating a microfluidic element, according to some embodiments of the present invention.

FIG. 3A is a schematic diagram illustrating a microfluidic element, according to some embodiments of the present invention. The microfluidic element 50 illustrated in FIG. 3A comprises an injection chamber 40A, a valve 70A, a transition chamber 517, a metering chamber 511A, a storage chamber 515A, an overflow chamber 513A, a collection chamber 516 and a reaction chamber 514A. This microfluidic element 50 may be configured on a circular microfluidic platform similar to the microfluidic platform 20 illustrated in FIG. 1A. For the embodied microfluidic platform 20 disclosed herein, the center of rotation 21 is defined as the interior of the microfluidic platform 20 and the circumference 22 is defined as the exterior of the microfluidic platform 20. The microfluidic element 50, from the interior to the exterior, comprises an injection chamber 40A, a valve 70A, a transition chamber 517, a metering chamber 511A, and a storage chamber 515A. An overflow chamber 513A and a collection chamber 516 are located at the left side and right side to the metering chamber 511A respectively and a reaction chamber 514A is further configured at the exterior side to the collection chamber 516. Several air vents 60 may be configured on the microfluidic element 50 for relieving the air pressure generated by the movement of sample in the microfluidic element 50. The sample flows into an enclosed chamber may confront resistance under some circumstances. The air vents are capable of decreasing regional air pressure and ease the resistance for a sample to flow into a chamber. Some exemplary air vents 60 are disposed on the transition chamber 517, the overflow chamber 513A, and the collection chamber 516 in FIG. 3A. Based on the requirement, the air vents may be disposed on the storage chamber 515A, the reaction chamber 514A, or other regions of a microfluidic element 50 in other embodiments.

The injection chamber 40A illustrated in FIG. 3A may be used to accommodate samples. The sample may be blood, urine, saliva, liquid water, or liquid food. The sample also may comprises high density substances and low density substances, such as the blood cells and the blood plasma in a blood sample, the urine protein and water in a urine sample, or the silt and water in a water sample obtained from a river.

The valve 70A illustrated in FIG. 3A is a capillary valve. However, a mechanical valve and other valves well-known in the art may be used in some other embodiments. The valve 70A is configured to prevent the sample from flowing into the transitional chamber 517 before a pre-determined condition is satisfied. For example, a capillary valve may constrain a sample by greatly increase the surface tension of the sample flowing by the capillary valve. Once the centripetal acceleration applied by the rotary unit 11 (as illustrated in FIG. 1B) reaches a threshold that the centrifugal force is higher than the surface tension and the capillary force, the sample would burst through the capillary valve and flow into the transition chamber 517.

The transition chamber 517 illustrated in FIG. 3A is configured to impede the sample from flowing into the metering chamber 511A. A sample flowing into the metering chamber 511A may confront resistance and sprinkle into other chambers uncontrollably if the volume of sample enters into the metering chamber 511A is greater than the volume of air expels from the microfluidic element 50. This may result in sample contamination and reduce the accuracy and specificity of the following assay.

The collection chamber 516 illustrated in FIG. 3A comprises an entry and an exit. The entry of the collection chamber 516 is connected with the metering chamber 511A and the exit is connected with the reaction chamber 514A. In particular, the collection chamber 516 has an entry with greater area and an exit with smaller area. The collection chamber 516 formed in a funnel-like shape may increase the efficiency on collecting sample from the metering chamber 511A and passing the sample into the reaction chamber 514A.

The reaction chamber 514A illustrated in FIG. 3A may be used to accommodate a test stripe (as illustrated in FIGS. 8A-8D) and perform in situ testing. The test strip 80 may, for example, be litmus papers, chlorine dioxide test strips, water hardness test strips, glucose test strips, ovulation test strips, colloid cold strips, Multistix® test strips, or other test strips well-known in the art.

The overflow chamber 513A illustrated in FIG. 3A may be used to accommodate sample overflowed from the metering chamber 511A. In some embodiments, the metering chamber 511A has a capacity to contain a first pre-determined volume of solution. Solution exceed the first pre-determined volume would flow from the metering chamber 511A to the overflow chamber 513A. Therefore, the overflow chamber 513A stabilizes the volume of sample in the metering chamber 511A in the first pre-determined volume by receiving an excessive amount of sample.

The overflow chamber 513A illustrated in FIG. 3A contains two small chamber connected by a capillary and forms a sandglass-like structure. The shrinking portion in the middle of a sandglass-like structure may obstruct the sample from reflowing back to the metering chamber 511A. The sandglass-like structure therefore increases the stability of sample volume metering of the microfluidic element 50.

The storage chamber 515A illustrated in FIG. 3A may be used to accommodate the high density substances segregated from the sample under the centrifugal force applied by the rotary unit 11 (as illustrated in FIG. 1B). Based on the multi-chamber structure of the microfluidic element 50, substances with different densities may be stored in the metering chamber 511A, the overflow chamber 513A, the storage chamber, and other chambers separately. The efficacy of sample preparation is therefore elevated. For example, the high density substances would be stored in the storage chamber 515A after centrifugation and the low density substances would remain in the metering chamber 511A. In some embodiments, the storage chamber 515A connects to the metering chamber 511A through a capillary. As the vibration unit 12 is activated, the capillary herein blocks the high density substances from moving back to the metering chamber 511A. The capillary may stabilize the volume and purity of sample in the metering chamber 511A and therefore increase accuracy of the assay performed on the microfluidic element 50.

The embodiments of FIG. 3A represents an exemplary microfluidic element 50 of the present invention. In some other embodiments, components of microfluidic elements may be fabricated in different arrangements, different conformations, and different compositions depending on the needs and consideration.

Figure 3B:
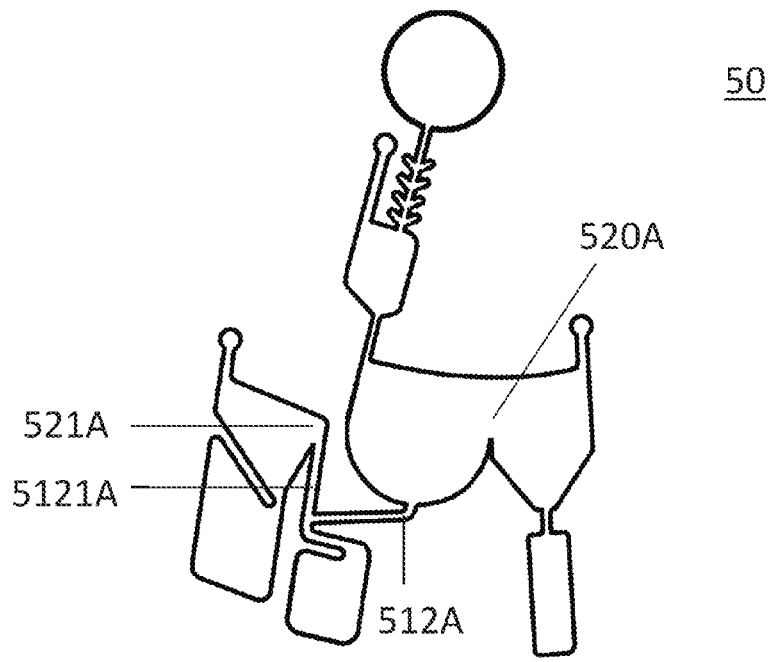
FIG. 3B is a schematic diagram illustrating the connections between the exemplary components of a microfluidic element, according to some embodiments of the present invention.

FIG. 3B is a schematic diagram illustrating the connections between the exemplary components of the microfluidic element illustrated in FIG. 3A. Though some components are not labeled with numerals, the microfluidic structure 50 in FIG. 3B illustrated each corresponding component in FIG. 3A including the injection chamber 40A, the valve 70A, the transition chamber 517, the metering chamber 511A, the storage chamber 515A, the overflow chamber 513A, a collection chamber 516, and a reaction chamber 514A. The two ends of the valve 70A are connected with the injection chamber 40A and the transition chamber 517 respectively, and the transition chamber 517 is further connected with the metering chamber 511A. The collection chamber 516 is connected with the metering chamber 511A. The collection chamber 516 also connects to the reaction chamber 514A at a first access 520A. The metering chamber 511A is connected to the overflow chamber 513A via a microfluidic channel 512A. The overflow chamber 513A and the microfluidic channel 512A are connected at a second access 521A. The microfluidic channel 512A further has an opening connected to the storage chamber 515A.

In some embodiments, the microfluidic channel 512A illustrated in FIG. 3B further comprises a turn 5121A. The turn 5121A may be in a crescent shape and is opening toward the center of rotation 21 (as illustrated in FIG. 1A) on the microfluidic platform 20. As the vibration unit 12 is activated, the turn 5121A may obstruct the sample in the overflow chamber 513A from reflowing back to the metering chamber 511A. The turn 2121A maintains the volume and purity of sample in the metering chamber 511A and therefore increase accuracy of the assay performed on the microfluidic element 50.

Figure 4A:
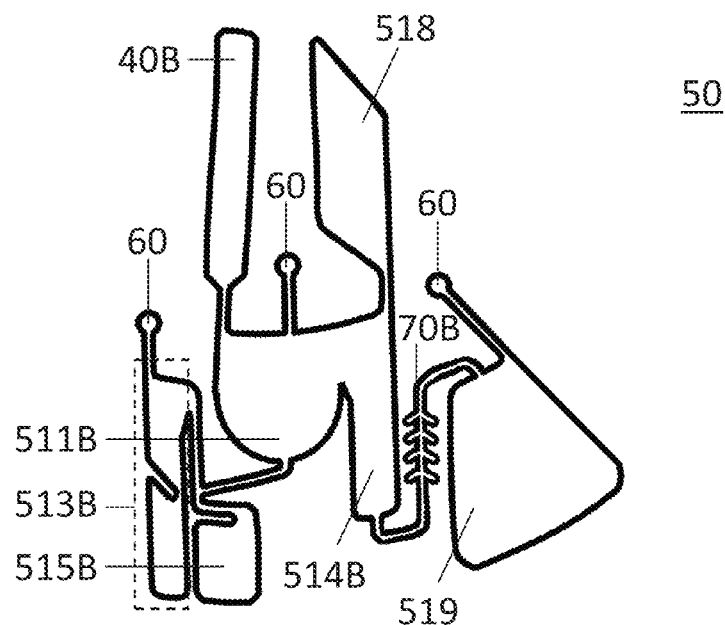
FIG. 4A is a schematic diagram illustrating a microfluidic element, according to some embodiments of the present invention.

FIG. 4A is a schematic diagram illustrating a microfluidic element, according to some embodiments of the present invention. The microfluidic structure 50 illustrated in FIG. 4 comprises an injection chamber 40B, a metering chamber 511B, a storage chamber 515B, an overflow chamber 513B, a solution chamber 518, a reaction chamber 514B, a valve 70B, and a waste chamber 519. This microfluidic element 50 may be provided on a circular microfluidic platform similar to the microfluidic platform 20 illustrated in FIG. 2A. For the embodied microfluidic platform 20 disclosed herein, the center of rotation 21 is defined as the interior of the microfluidic platform 20 and the circumference 22 is defined as the exterior of the microfluidic platform 20. The microfluidic element 50, from the interior to the exterior, comprises the injection chamber 40B, the metering chamber 511B, and the storage chamber 515B. The overflow chamber 513B and the reaction chamber 514B are provided at the left side and the right side to the metering chamber 511B respectively. For the reaction chamber 514B, the solution chamber 518 is configured at the interior side and the waste chamber 519 is configured at the exterior side or an adjacent place. The valve 70B is connected between the reaction chamber 514B and the waste chamber 519.

Figure 8A:
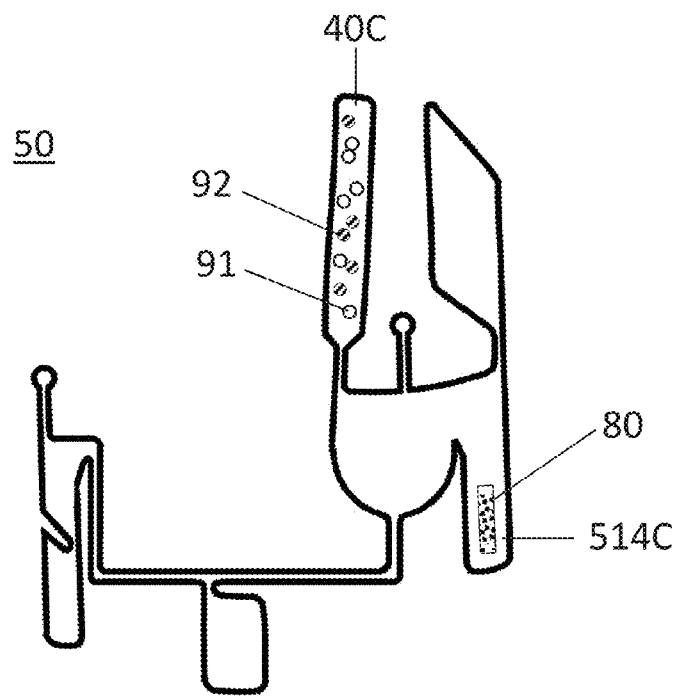
FIGS. 8A-8D is schematic diagrams illustrating the steps of a method for operating microfluidic devices, according to some embodiments of the present invention.

The solution chamber 518 illustrated in FIG. 4A may be used to accommodate solution. The solution may enter the reaction chamber 514B without passing through several components in the microfluidic element 50. The solution injected into the solution chamber 518 may, for example, be a buffer solution, a wash buffer, a reagent, or a solvent. For instance, the test strip 80 (as illustrated in FIG. 8A) may be preserved in an inactive form, and an activator in the solution chamber 518 may flow into the reaction chamber 514B to activate the test strip 80 during an assay. In another instance, a wash buffer in the solution chamber 518 may flow into the reaction chamber 514B to rinse the test strip 80 after the reaction is ended. In yet another example, the test strip 80 used for testing is a chromatography paper strip, and a buffer in the solution chamber 518 may flow into the reaction chamber 514B under the centrifugal force applied by the activated rotary unit 11 (as illustrated in FIG. 1B) to drive the chromatography.

The waste chamber 519 illustrated in FIG. 4A may be used to accommodate the solution expelled from the reaction chamber 514B. Under some cases, a false positive diagnose may be yielded once the sample retained in the reaction chamber 514B long enough to saturated the reaction of the test strip 80 (as illustrated in FIG. 8A). Under some other cases, the sample and solution retained in the reaction chamber 514B may mask signals on the test strip and raise the difficulty in obtaining results by the detection module 30 (as illustrated in FIG. 1B). Under above situations, a waste chamber 519 may be provided to absorb the sample and solution expelled from the reaction chamber 514B.

The valve 70B illustrated in FIG. 4A is a capillary valve and could be used to control the flow velocity of solution. However, a mechanical valve and other valves well-known in the art may be used in other embodiments. Under some situations, an incomplete reaction may be yielded once the sample or solution in the reaction chamber 514B fled into the waste chamber 519 without any resistance. Under above situations, a valve 70B may be provided to slow down the flow velocity and decline the possibility that solution left the reaction chamber 514B before the reaction of the test strip 80 is ended The embodiments of FIG. 4A represents an exemplary microfluidic element 50 of the present invention. In some other embodiments, components of microfluidic elements may be fabricated in different arrangements, different conformations, and different compositions depending on the needs and consideration.

Figure 4B:
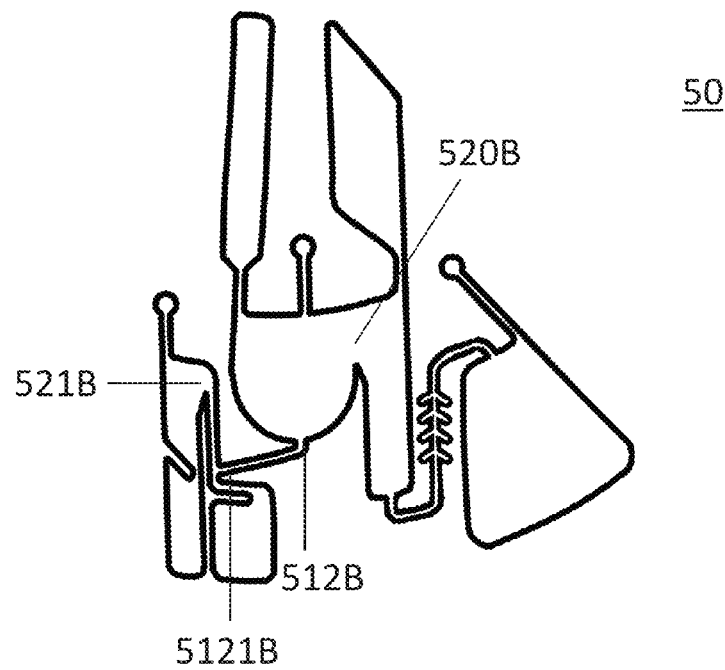
FIG. 4B is a schematic diagram illustrating the connections between the exemplary components of a microfluidic element, according to some embodiments of the present invention.

FIG. 4B is a schematic diagram illustrating the connections between the exemplary components of the microfluidic element illustrated in FIG. 4A. Though some components are not labeled with numerals, the microfluidic structure 50 in FIG. 4B illustrated each corresponding component in FIG. 4A including the injection chamber 40B, the metering chamber 511B, the storage chamber 515B, the overflow chamber 513B, a solution chamber 518, a reaction chamber 514A, a valve 70B, and a waste chamber 519. The injection chamber 40B is provided at the interior side to the metering chamber 511B and connected with the metering chamber 511B. The left side and the right side of the metering chamber 511B are connected with the overflow chamber 513B and the reaction chamber 514B respectively. The connection between the metering chamber and the reaction chamber is defined as a first access 520B. The solution chamber 518 illustrated in FIG. 4B is located at the interior side to the reaction chamber 518B and is connected with the reaction chamber 518B. The waste chamber 519 is configured at the exterior side or an adjacent place to the reaction chamber 514B, and the valve 70B is connected between the reaction chamber 514B and the waste chamber 519. On the other hand, the metering chamber 511B is connected to the overflow chamber 513B via a microfluidic channel 521B, and the connection between the microfluidic channel 512B and the overflow chamber 513B is defined as a second access 521B. In FIG. 4B, the microfluidic channel 512B comprises a turn 5121B. A passage linked with the storage chamber 515B is further protruding from the turn 5121B in some embodiments.

Figure 5:
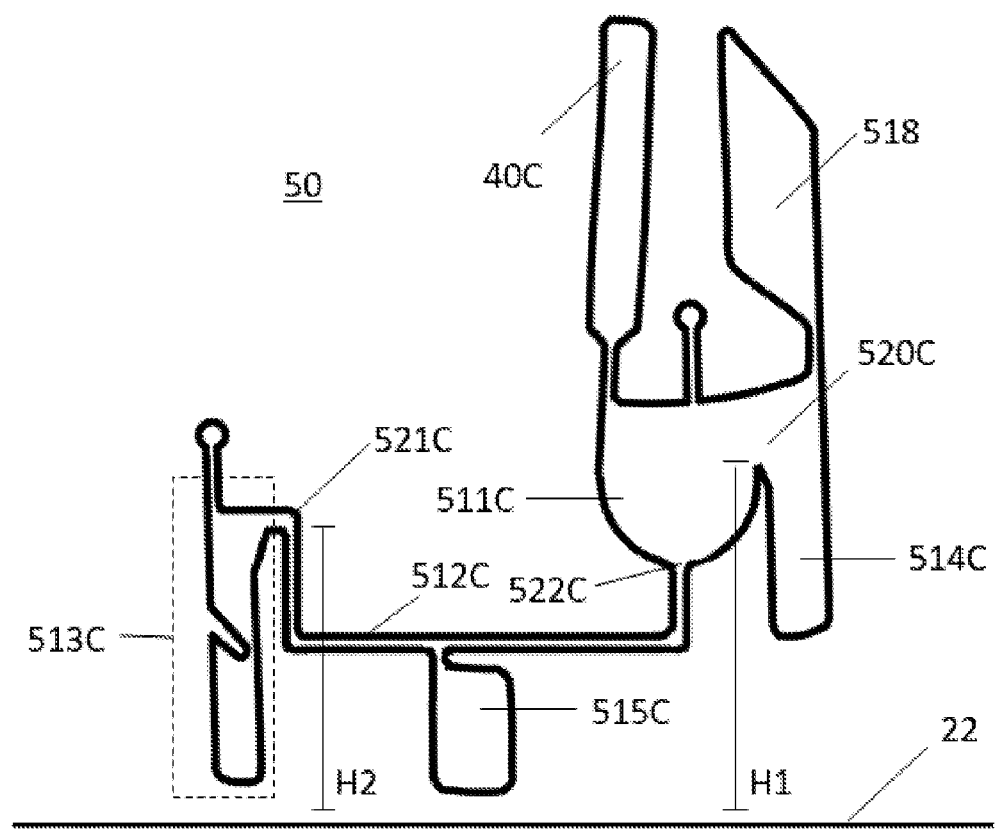
FIG. 5 is a schematic diagram illustrating the configurations of the exemplary components of a microfluidic element, according to some embodiments of the present invention.

FIG. 5 is a schematic diagram illustrating the configurations of the exemplary components of a microfluidic element, according to some embodiments of the present invention. The microfluidic element 50 illustrated in FIG. 5 comprises an injection chamber 40C, a metering chamber 511C, a storage chamber 515C, an overflow chamber 513C, a solution chamber 518, and a reaction chamber 514C. In particular, the connection site between the metering chamber 511C and the reaction chamber 514C is defined as a first access 520C, and the connection sites between the overflow chamber 513C, the metering chamber 511C, and the microfluidic channel 512C is defined as a second access 521C and a third access 522C respectively.

The microfluidic element 50 illustrated in FIG. 5 is configured between the center of rotation 21 and the circumference 22 of a circular microfluidic platform similar to the microfluidic platform 20 illustrated in FIG. 2A. To disclose some features in these embodiments, the circumference 22 herein which should be a curve line is illustrated as a straight line. The first distance H1 represents the distance between the circumference 22 and the first access 520C, and the second distance H2 represents the distance between the circumference 22 and the second access 521C. The first distance H1 is equal to or longer than the second distance H2. Based on that the microfluidic element 50 is disposed on a circular microfluidic platform 20, the distance between the center of rotation 21 and the first access 520C is equal to or shorter than the distance between the center of rotation 21 and the second access 521C. Accordingly, differences between the centrifugal potential energies at the first access 520C and the second access 521C favor the sample in the metering chamber 511C to flow, under the centrifugal force applied by the activated rotary unit 11 (as illustrated in FIG. 1B), preferably to the overflow chamber 513C rather than the reaction chamber 514C. In some alternate embodiments, capacity of the metering chamber 511C may be regulated by modifying the first distance H1 and the second distance H2.

Figure 6:
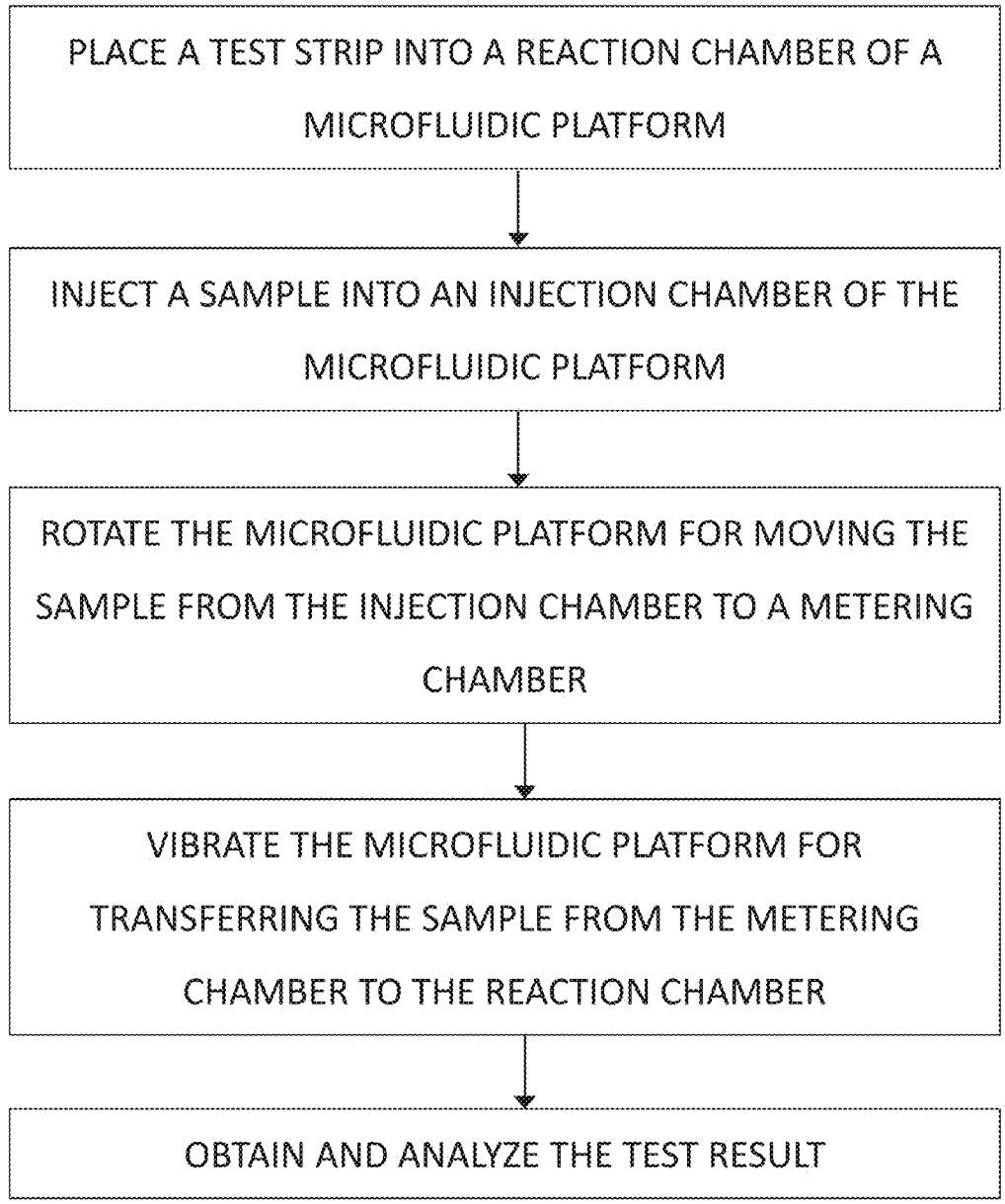
FIG. 6 is a flow diagram illustrating a method for operating microfluidic devices, according to some embodiments of the present invention.

FIG. 6 is a flow diagram illustrating a method for operating microfluidic devices, according to some embodiments of the present invention. The method begins with placing a test strip into a reaction chamber of a microfluidic platform and injecting a sample into an injection chamber on the same microfluidic platform. The microfluidic platform then rotates to transfer the sample in the injection chamber to a metering chamber. The microfluidic platform subsequently vibrates to move the sample in the metering chamber to the reaction chamber. The result presented on the test strip in the reaction chamber is obtained manually or automatically by the detection module after the reaction between the sample and the test strip is ended.

A microfluidic device, combining the microfluidic element 50 illustrated in FIG. 3A to the microfluidic device illustrated in FIG. 1B, is provided as an exemplary device to demonstrate the method for operating microfluidic devices. In the first step, a sample and a test strip 80 (as illustrated in FIG. 8A) are placed into the injection chamber 40A and the reaction chamber 514A of the microfluidic platform 20 respectively. The microfluidic platform 20 is then rotated to pass the sample from the injection chamber 40A to the metering chamber 511A. The microfluidic platform 20 is subsequently vibrated to move the sample in the metering chamber 511A to the reaction chamber 514A. Finally, the result presented on the test strip 80 is obtained manually or automatically by the detection module 30 after the reaction between the sample and the test strip 80 in the reaction chamber 514A is ended.

In some embodiments of FIG. 6, the microfluidic platform used to perform the method further comprises an overflow chamber connected with the metering chamber. A portion of the sample entered the metering chamber would flow further into the overflow chamber and volume of the sample in the metering chamber is maintained in a first pre-determined volume. The first pre-determined volume is, used the microfluidic element 50 illustrated in FIG. 5 as an example, associated with the size of the metering chamber 511C and the distance H2 between the circumference 22 and the second access 521C.

In the embodiment of FIG. 6, a vibration condition, comprising the vibration frequency and vibration amplitude, is determined before the step of vibrating the microfluidic platform. A second pre-determined volume of sample would be transferred to the reaction chamber under the vibration condition. The second pre-determined volume is positively correlated to the vibration frequency, the vibration amplitude, and volume of the sample in the metering chamber. However, the second pre-determined volume is negatively correlated to the viscosity index of sample.

Figure 7A:
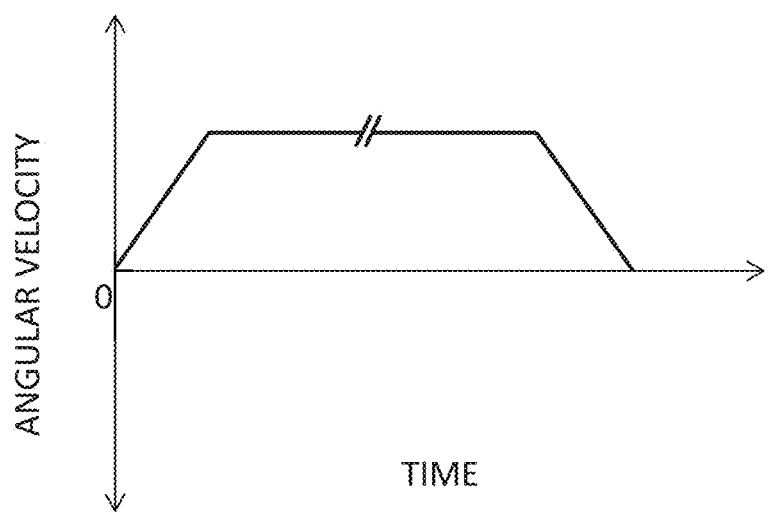
FIG. 7A is a graph illustrating the change in angular velocity over time of an exemplary rotary unit, according to some embodiments of the present invention.
Figure 7B:
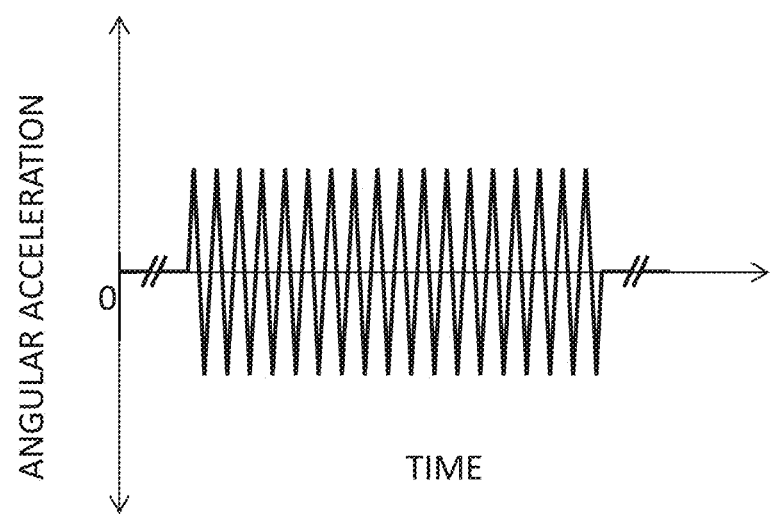
FIG. 7B is a graph illustrating the change in angular acceleration over time of a vibration unit, according to some embodiments of the present invention.

FIG. 7A is a graph illustrating the change in angular velocity over time of an exemplary rotary unit, according to some embodiments of the present invention. The drive module illustrated in FIG. 1B drives the microfluidic platform 20 to rotate once the rotary unit 11 is activated to generate centrifugal force. FIG. 7B is a graph illustrating the change in angular acceleration over time of a vibration unit, according to some embodiments of the present invention. The drive module illustrated in FIG. 1B drives the microfluidic platform 20 to vibrate once the vibration unit 11 is activated to vibrate the microfluidic platform 20 by vibrating, shaking, switching repeatedly between positive/negative angular velocities, or switching repeatedly between positive/negative angular accelerations.

Figure 8B:
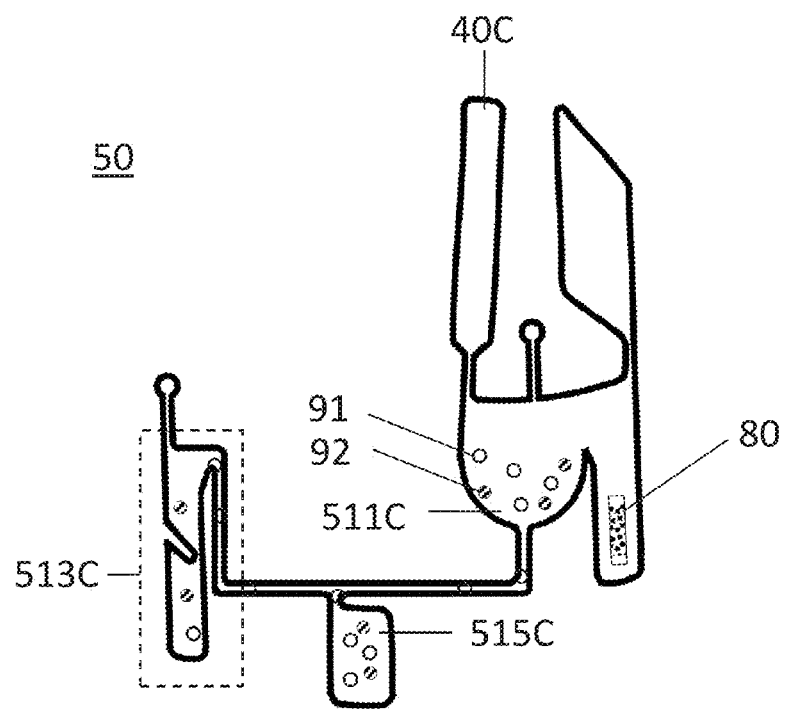
Figure 8C:
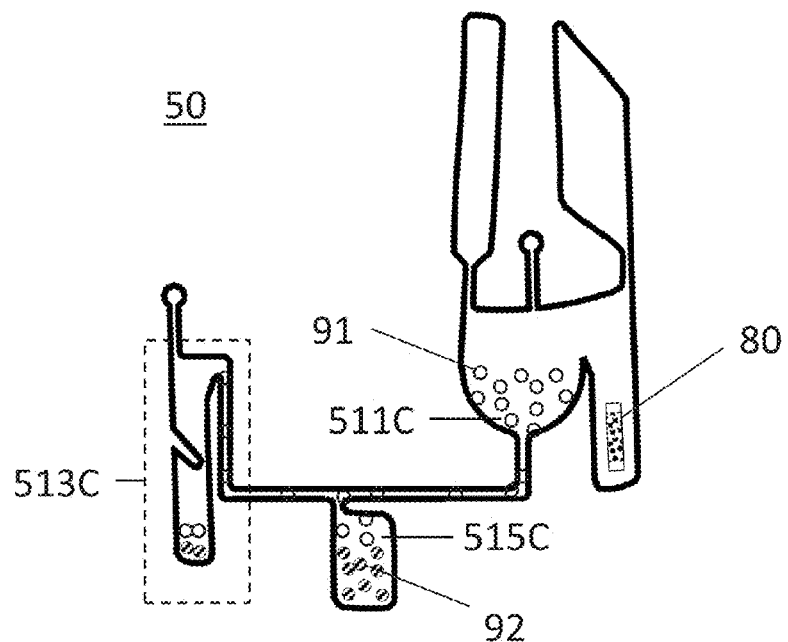
Figure 8D:
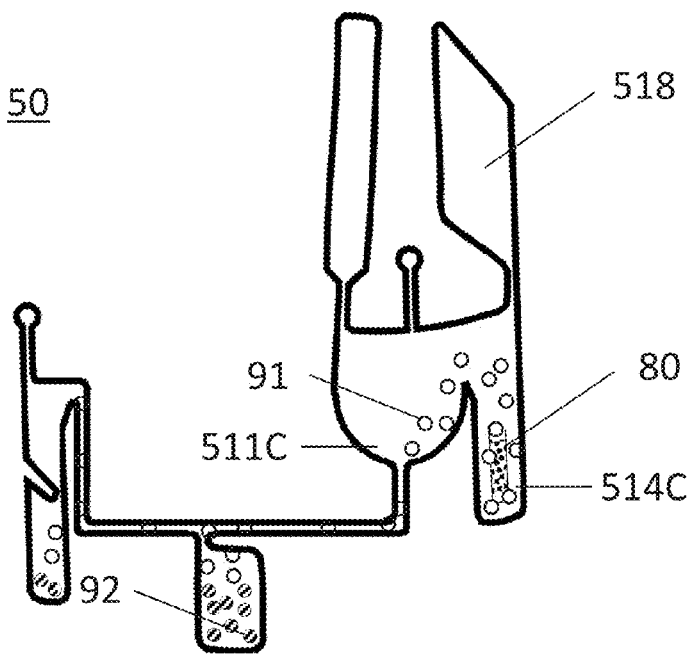

FIGS. 8A-8D is schematic diagrams illustrating the steps of methods for operating microfluidic devices, according to some embodiments of the present invention. The microfluidic device used in FIGS. 8A-8D is similar to the microfluidic device illustrated in FIG. 1B with the microfluidic element 50 in FIG. 5. As illustrated in FIG. 8A, a test strip 80 is laid into the reaction chamber 514C and a sample is injected into the injection chamber 40C before an assay is performed on a microfluidic platform 20. The sample injected in comprises low density substances 91 and high density substances 92. In FIG. 8B, the rotary unit 11 of the drive module 10 is activated to elevated the angular velocity and forces both the low density substances 91 and high density substances 92 in the sample to flow into the metering chamber 511C and the storage chamber 515C. Volume of the sample in the metering chamber 511C is maintained in a first pre-determined volume by overflowing the excessive sample into the overflow chamber 513C. The overflow chamber 513C therefore prevents the metering chamber 511C from being overfilled and spilling the sample to the reaction chamber 514C. In FIG. 8C, substances in the sample are aligned in the microfluidic element 50 based in part on the density gradient under the centrifugal force applied by the rotary unit 11. In particular, the high density substances 92 are mostly located at the exterior region, the storage chamber 515C, and the low density substances 91 are mostly located at the interior region, the metering chamber 511C, on the microfluidic platform 20. As in FIG. 8D, part of the sample in the metering chamber 511C is transferred to the reaction chamber 514C to interact with the test strip 80 by the vibration unit 12 in the drive module 10.

Some embodiments of FIGS. 8A-8D relates to the methods for investigating milk quality on the microfluidic platform 20 illustrated in FIG. 2B. The microfluidic platform 20 has integrated microfluidic elements which comprise an injection chamber 40', an injection port 41, eight sub-chambers 42, and eight microfluidic elements 50. In the first step, the eight reaction chambers 514C on the microfluidic platform 20 each accommodates a glucose test strips, a lactoprotein test strip, a pH test strip, a calcium test strip, a tetracycline test strip, a chloramphenicol test strip, and a β-lactam test strip respectively, and 210 μL of milk is injected into the injection chamber 40' for the investigation. Angular velocity of the microfluidic platform 20 is then accelerated to 600 RPM by the rotary unit 11 of the drive module 10 and the milk subsequently splits up and flows into eight microfluidic elements 50. Since each of the metering chambers 511C is designed to accommodate 25 μL of milk, the milk exceeded this capacity will overflow into the storage chamber 515C and the overflow chamber 513C. With three minutes at 600 RPM, substances such as the microbes and coagula in the milk are moved to the storage chamber 515C due to the centrifugal force applied by the rotary unit 11, and the lactoproteins and substances with low sedimentation coefficients are retained in the metering chamber 511C. In the last step, the vibration unit 12 of the drive module 10 vibrates in a vibration condition, which is at amplitude of 720 degree and frequency of 10 Hz, to transfer the milk in the metering chamber 511C to the reaction chamber 514C to initiate reactions with the test strip 80.

Some embodiments of FIGS. 8A-8D relates to the methods for investigating triglycerides levels in blood samples on the microfluidic platform 20 illustrated in FIG. 2A. The microfluidic platform 20 has eight isolated microfluidic elements 50. In the first step, 300 μL of blood samples obtained from eight different subjects were injected into the eight injection chamber 40C respectively. Each of the eight reaction chambers 514C accommodates a triglycerides strip. The actual sample volume in each injection chamber is ranging from 280 μL to 32 μL individually since the manual injection is highly unstable and has an about 5% volume variation. Angular velocity of the microfluidic platform 20 is then accelerated to 5000 RPM by the rotary unit 11 of the drive module 10 and the blood samples are subsequently flow into the microfluidic elements 50 respectively. In this stage, each metering chambers 511C contains an equal volume of blood sample since the metering chambers 511C are designed to accommodate 250 μL of blood sample individually. The blood sample exceeded this 25 μL capacity will overflow into the storage chamber 515C and the overflow chamber 513C. With 90 seconds at 5000 RPM, substances such as the blood cells and coagula in the blood sample are moved to the storage chamber 515C due to the centrifugal force applied by the rotary unit 11, and the plasma is retained in the metering chamber 511C. In the last step, the vibration unit 12 of the drive module 10 vibrates at amplitude of 720 degree and frequency of 15 Hz to transfer 100 μL of the plasma in the metering chamber 511C to the reaction chamber 514C to initiate reactions with the test strip 80.

Some embodiments of FIGS. 8A-8D relates to the methods for investigating pathogens in a blood sample on the microfluidic platform 20 illustrated in FIG. 2B. The microfluidic platform 20 has integrated microfluidic elements which comprise an injection chamber 40', an injection port 41, eight sub-chambers 42, and eight microfluidic elements 50. In the first step, the eight reaction chambers 514C on the microfluidic platform 20 each accommodates an HBs Ag test strip, an HCV Ab cassette, a Syphilis test cassette, an HIV test cassette, a *Salmonella* Ag test strip, a Malaria Ag test cassette, a *Mycoplasma* IgG test strip, and an *H. pylori* IgG test strip respectively, and 680 μL of blood sample is injected into the injection chamber 40' for the investigation. Angular velocity of the microfluidic platform 20 is then increased to 600 RPM by the rotary unit 11 of the drive module 10 and the blood sample is distributed to eight sub-chambers 42 equally. The rotary unit 11 drives the rotation speed further to 5000 RPM, the burst frequency of the valves (as illustrated in FIG. 2B) connected between the sub-chambers 42 and the metering chambers 511C in these embodiments, to allow the blood samples in each sub-chambers 42 to flow into the metering chambers 511C respectively. Since each of the metering chambers 511C is designed to accommodate 80 μL of blood sample, the blood sample exceeded this capacity will overflow into the storage chamber 515C and the overflow chamber 513C. With 90 seconds at 5000 RPM, high density substances such as the blood cells and coagula in the blood sample are moved to the storage chamber 515C due to the centrifugal force applied by the rotary unit 11, and low density substances such as the plasma are retained in the metering chamber 511C. In the last step, the vibration unit 12 of the drive module 10 vibrates for 15 seconds at amplitude of 1080 degree and frequency of 5 Hz to transfer 3.50 μL of the plasma in the metering chamber 511C to the reaction chamber 514C to initiate reactions with the test strip 80.

In some alternate embodiments, the microfluidic elements 50 on a microfluidic platform 20 may have different conformations. For instance, the Syphilis test cassette and HIV test cassette are recommended to be used with whole blood, but the *H. pylori* IgG test strip and *Mycoplasma* IgG test strip are recommended to be used with plasma. For performing these assays simultaneously, a customized microfluidic platform 20 comprising several microfluidic elements 50 with the storage chamber 515C and several microfluidic elements 50 without the storage chamber may be employed.

Some embodiments of FIGS. 8A-8D relates to the methods for screening the presence of drugs in a urine samples on the microfluidic platform 20 illustrated in FIG. 2A. The microfluidic platform 20 has eight isolated microfluidic elements 50. Each injection chamber 40C on the microfluidic platform 20 contains 3 drops of the urine sample from a subject. The eight reaction chambers 514C each accommodate one type of colloidal cold tests, which are the morphine test strip, the heroin test strip, the MDMA test strip, the cocaine test strip, the amphetamine test strip, the methamphetamine test strip, the THC test strip, and the valium test strip respectively. Since the dropper used to inject the urine sample provides very low volume stability, the actual sample volume in each injection chamber is ranging from 15 μL to 200 μL individually. Angular velocity of the microfluidic platform 20 is then accelerated to 5000 RPM by the rotary unit 11 of the drive module 10 and the urine samples subsequently flow into the microfluidic elements 50. Each of the metering chambers 511C in this stage contains an equal volume of urine sample, since the metering chambers 511C are designed to accommodate 13 μL of urine sample respectively. The blood sample exceeded this capacity will automatically overflow into the storage chamber 515C and the overflow chamber 513C. With 120 seconds at 12000 RPM, substances such as urine proteins are moved to the storage chamber 515C due to the centrifugal force applied by the rotary unit 11, and the supernatant is retained in the metering chamber 511C. In the last step, the vibration unit 12 of the drive module 10 vibrates for 10 seconds at amplitude of 180 degree and frequency of 30 Hz to transfer 5.5 μL of the supernatant in the metering chamber 511C to the reaction chamber 514C to initiate reactions with the test strip 80.

In some alternate embodiments, the methods further comprise steps for introducing a solution into the reaction chamber 514C. For instance, some test strips may react incompletely due to that the urine samples have different natures. Under the circumstance, a step for introducing 15 μL of wash buffer to the solution chamber 518 may be comprised in the methods to rinse the test strips 80 in the reaction chamber 514C.

Figure 9:
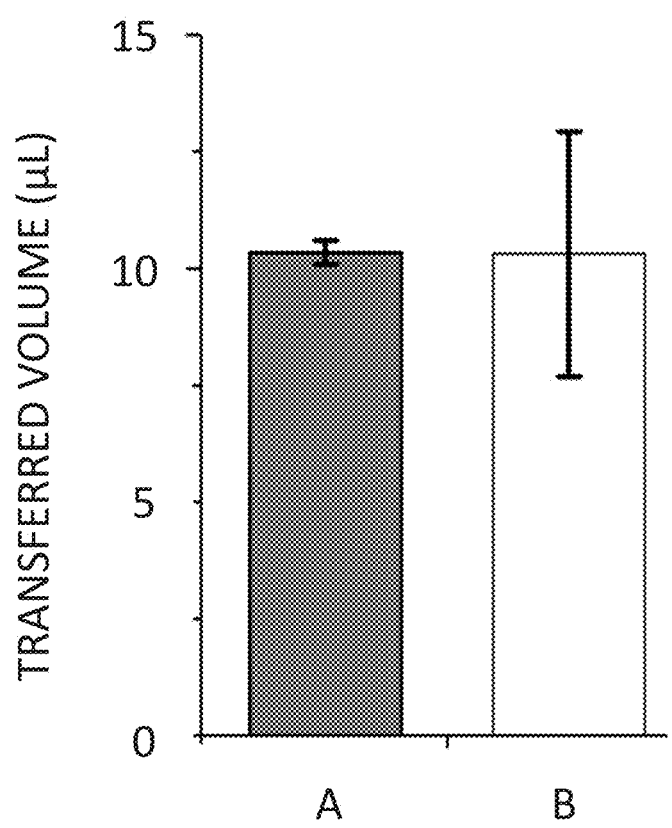
FIG. 9 is a bar chart illustrating the result of stability test, according to some embodiments of the present invention.

FIG. 9 is a bar chart illustrating the result of stability test, according to some embodiments of the present invention. The stability test examined the effects of an overflow chamber on the sample volumes transfer from the metering chamber to the reaction chamber. Conformations of the two microfluidic elements in the stability test are similar to the microfluidic element 50 illustrated in FIG. 3A. The microfluidic element A is a microfluidic element 50 with the overflow chamber 513A, and the microfluidic element B is a microfluidic element 50 without the overflow chamber 513A. The results indicated that the microfluidic element A shows an about 3% variation and the microfluidic element B shows an about 25% variation when compared to 10 μL, the pre-determined volume, according to FIG. 9. The results suggest that, compared to the microfluidic element 50 without the overflow chamber 513A, the microfluidic element 50 with the overflow chamber 513A has better stability. The microfluidic element 50 without the overflow chamber 513A may further incorporate other stabilization elements or use precise volumetric measurements in advance to elevate the stability.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A microfluidic device, comprising:
   a drive module, containing a rotary unit and a vibration unit; and
   a microfluidic platform, mounting on the drive module, controlled by the rotary unit and the vibration unit, wherein the microfluidic platform contains a center of rotation and at least one microfluidic element, and wherein each microfluidic element further comprises:
   an injection chamber, for accommodating a sample;
   a metering chamber, connected with the injection chamber; and
   a reaction chamber, connected with the metering chamber located on the outside of the metering chamber;
   wherein the vibration unit is configured to drive the microfluidic platform to vibrate, shake and repeatedly switching between clockwise and counterclockwise rotations, so that the sample in the metering chamber is transferred to the reaction chamber.

2. The microfluidic device according to claim 1, wherein the microfluidic platform contains multiple microfluidic elements, and wherein at least two injection chamber are integrated with each other.

3. The microfluidic device according to claim 1, wherein each microfluidic element further comprises:
   an overflow chamber; and
   a microfluidic channel, connected between the metering chamber and the overflow chamber.

4. The microfluidic device according to claim 3, wherein the metering chamber and the reaction chamber are connected at a first access, and wherein the microfluidic channel is connected to the overflow chamber and the metering chamber at a second access and a third access respectively, and wherein the distance from the center of rotation to the first access is smaller than the distances from the center of rotation to both the second access and the third access.

5. The microfluidic device according to claim 3, wherein each microfluidic element further comprises a storage chamber connected with the microfluidic channel.

6. The microfluidic device according to claim 1, wherein each microfluidic element further comprises a collection chamber configured between the metering chamber and the reaction chamber, and wherein the collection chamber contains:
   an entry, connected with the metering chamber; and
   an exit, connected with the reaction chamber;
   and wherein the area of the entry is greater than the area of the exit.

7. The microfluidic device according to claim 1, wherein the microfluidic element further comprises a waste chamber connected with the reaction chamber.

* * * * *